United States Patent [19]

Schuhmacher et al.

[11] 4,146,547
[45] Mar. 27, 1979

[54] MANUFACTURE OF BZ-1-BROMOBENZANTHRONE

[75] Inventors: Alfred Schuhmacher, Ludwigshafen; Karl-Erich Kling, Frankenthal, both of Fed. Rep. of Germany

[73] Assignee: BASF Aktiengesellschaft, Ludwigshafen, Fed. Rep. of Germany

[21] Appl. No.: 811,463

[22] Filed: Jun. 30, 1977

[30] Foreign Application Priority Data

Jul. 15, 1976 [DE] Fed. Rep. of Germany ....... 2631833

[51] Int. Cl.$^2$ .............................................. C09B 3/08
[52] U.S. Cl. .................................................... 260/364
[58] Field of Search ......................................... 260/364

[56] References Cited

U.S. PATENT DOCUMENTS

| 1,851,019 | 3/1932 | Murch | 260/364 |
| 2,563,663 | 8/1951 | Sievenpiper | 260/364 |

FOREIGN PATENT DOCUMENTS 193959  8/1906  Fed. Rep. of Germany ........... 260/364

Primary Examiner—Allen B. Curtis
Assistant Examiner—Raymond Covington
Attorney, Agent, or Firm—Keil & Witherspoon

[57] ABSTRACT

A process for the manufacture of Bz-1-bromobenzanthrone by brominating finely divided benzanthrone in aqueous suspension, wherein the improvement comprises treating benzanthrone having a mean particle size of 30 μm or less with bromine or brominating agent at above 80° C.

A product which contains from 91 to 94% by weight of Bz-1-bromobenzanthrone is obtained.

10 Claims, No Drawings

MANUFACTURE OF BZ-1-BROMOBENZANTHRONE

The present invention relates to a process for the manufacture of Bz-1-bromobenzanthrone by brominating benzanthrone.

Bz-1-Bromobenzanthrone, hereinafter also referred to as bromobenzanthrone, is as a rule manufactured by brominating benzanthrone. Depending on the process conditions, varying amounts of Bz-1,6-dibromobenzanthrone are formed in this method.

It is known to brominate benanthrone in glacial acetic acid (German Patent No. 193,959) or in high-boiling organic liquids which are inert under the reaction conditions, e.g. nitrobenzene (German Patent No. 516,535). These processes suffer from the disadvantage that the mother liquor of the bromination mixture must be worked up and the liquids must be regenerated. As a result, these processes are expensive and uneconomical.

German Patent No. 595,461 discloses the bromination of benzanthrone in chlorosulfonic acid in the presence of sulfur. Apart from the fact that the bromination product is contaminated with sulfur, this process does not give a defined product.

BIOS Final Report No. 897, page 71, discloses the manufacture of Bz-1-bromobenzanthrone by heating finely divided benzanthrone, which has been obtained by dissolution in sulfuric acid and reprecipitation, in a mixture of aqueous dilute hydrochloric acid, chloroacetic acid mother liquor and bromine, at 70° C. The hydrogen bromide formed during the bromination can be utilized for the bromination by adding oxidizing agents, e.g. sodium hypochlorite solution.

The bromobenzanthrone thus obtained contains not only unreacted benzanthrone but also substantial amounts of dibromobenzanthrone, which is a disadvantage as regards the use of the product as a dye intermediate. Furthermore, the presence of organic substances in the mother liquor is undesirable for ecological reasons, i.e. because it pollutes the effluent.

We have found that Bz-1-bromobenzanthrone is obtained in excellent yield and good purity by brominating finely divided benzanthrone with brominating agents in aqueous suspension if bromine or the brominating agent is allowed to act on benzanthrone having a mean particle size of 30 $\mu$m or less, suspended in water, at above 80° C., using a molar ratio of bromine or brominating agent to benzanthrone of approximately 1:1.

The process gives a product which contains from 91 to 94 percent by weight of Bz-1-bromobenzanthrone, in addition to from 1.5 to 3 per cent by weight of dibromobenzanthrone and from 2 to 4 per cent by weight of benzanthrone.

In general, the process of the invention is carried out by suspending the finely divided benzanthrone in water, heating the suspension to 80° C. or above, and then adding the bromine or brominating agent uniformly over a period of from 1 to 4 hours, whilst keeping the temperature at above 80° C. After completion of the reaction, the product is isolated and washed with water until it is neutral.

The finely divided benzanthrone can be obtained by various methods, e.g. by dissolving benzanthrone in sulfuric acid, precipitating the solution by adding it to a large amount of water, filtering off the precipitated product and washing it until neutral. It is also possible to mill a slurry of benzanthrone in water in a ball mill until the required finely divided state is reached. Advantageously, the benzanthrone is finely divided by milling the aqueous suspension in a continuous mill, e.g. a sand mill or bead mill. The rate at which the suspension passes through the mill is set so that the milled material which issues has a mean particle size of 30 $\mu$m or less. It is also possible to comminute the dry benzanthrone to the requisite particle size in a suitable mill. If suspensions with particles of mean size greater than 30 $\mu$m are used, the results obtained are less good. Preferably, a milled material with a mean particle size of from 20 to 30 $\mu$m is employed. The suspension contains from 5 to 20, preferably from 10 to 15, per cent by weight, based on suspension, of finely divided benzanthrone. In addition to the finely divided state of the benzanthrone, it is above all the temperature at which the brominating agent is added which is an important factor in the success of the process of the invention; the brominating agent is added at from 80° C. to the boiling point of the aqueous suspension, preferably at from 85° to 95° C. The process can also be carried out under pressure at above the boiling point of water, e.g. at up to 120° C. Since this requires pressure-resistant vessels and there is not other advantage in working at the higher temperature, the bromination is preferably carried out at from 85° to 95° C. The importance of the temperature at which the brominating agent is added may be seen from the following: if bromine is added slowly at room temperature to a fine aqueous suspension of benzanthrone, of from 5 to 10 percent strength by weight, and the mixture is then heated to 85° C., the product obtained contains from 71 to 74 percent by weight of Bz-1-bromobenzanthrone, from 10 to 13 percent by weight of dibromobenzanthrone and from 10 to 13 percent by weight of starting material.

If the bromine is added to the same suspension which has, however, been heated to 85° C., the product obtained contains from 91 to 94 percent by weight of Bz-1-bromobenzanthrone in addition to from 1.5 to 3 percent by weight of dibromobenzanthrone and from 2 to 4 percent by weight of benzanthrone.

The bromination may be carried out either with molecular bromine or with brominating agents. Examples of the latter, for the purposes of the invention, are bromides and oxidizing agents. Examples of suitable oxidizing agents are alkali metal hypochlorites, e.g. sodium hypochlorite or potassium hypochlorite or, preferably, molecular chlorine. The bromides used are preferably the alkali metal bromides or alkaline earth metal bromides. The amount of bromine required in the process according to the invention is about 1 mole per mole of benzanthrone or, when using bromide and oxidizing agent, about 1 equivalent of bromide and at least 1 equivalent of oxidizing agent per mole of benzanthrone.

The process can also be carried out by only adding ½ mole of bromine per mole of benzanthrone at above 80° C. and then oxidizing the hydrogen bromide formed (i.e. the bromide ions present in the solution) to bromine by passing chlorine into the mixture, and thus completing the bromination. Any possible excess of chlorine in the aqueous phase is not detrimental under the stated conditions. The product obtained has the same composition as that obtained by using 1 mole of bromine per mole of benzanthrone.

It is known that the action of molecular bromine on benzanthrone at room temperature results in brown adducts which, on heating at above 80° C., decompose into bromobenzanthrone and hydrogen bromide. Furthermore, it has been disclosed that the bromide adduct very readily adds further bromine at room temperature. The compounds thus obtained, on scission - which occurs at from 80° C. upwards — give more highly brominated benzanthrones. It is due to this that even if less than an equivalent amount of bromine is added, subsequent heating at 80° C. gives a bromobenzanthrone with varying amounts of dibromobenzanthrone and starting compound.

The result of the process according to the invention was not to be expected since as a rule monosubstitution takes place preferentially in the bromination at lower temperatures and polysubstitution takes place preferentially in the bromination at higher temperatures.

The invention is further illustrated by the following Examples in which parts are by weight.

EXAMPLE 1

121 parts of pure benzanthrone having a mean particles size of from 20 to 30 $\mu$m are stirred into 700 parts of water. The suspension is brought to 92° C. by directly introducing steam. At this temperature, 90 parts of bromine are run in uniformly over 3 hours. The mixture is then stirred for a further 2 hours at 85° C. and is filtered on a filter press, and the product is washed with water until neutral.

The yield is 155 parts.

The reaction product has the following composition: 93% of Bz-1-bromobenzanthrone, 3.0% of dibromobenzanthrone and 4% of benzanthrone.

EXAMPLE 2

121 parts of pure benzanthrone (mean particle size 30 $\mu$m) are suspended in 1,800 parts of water. After heating the mixture to 90° C., 45 parts of bromine are run in over 2 hours, whilst stirring. 23 parts of chlorine gas are then passed into the suspension over 4 hours at 85° C. After this, the reaction is complete. The mixture is filtered and the product is washed until neutral.

The yield is 156 parts.

The reaction product has the following composition: 92% of Bz-1-bromobenzanthrone, 4% of dibromobenzanthrone and 4% of benzanthrone.

We claim:

1. In a process for the manufacture of Bz-1bromobenzanthrone by brominating finely divided benzanthrone with bromine or a brominating agent in aqueous suspension, the improvement which comprises:
   suspending benzanthrone which has a mean particle size of 30 $\mu$m or less in a single reaction medium consisting essentially of water;
   heating the suspension to 80° or above; and
   then adding said bromine or brominating agent gradually to the suspension maintained at a temperature above 80° C., the molar ratio of the added bromine or brominating agent to benzanthrone being approximately 1:1, thereby resulting in yields of Bz-1-Bromobenzanthrone of at least about 91%.

2. A process as claimed in claim 1, in which the mean particle size is from 20 to 30 $\mu$m.

3. A process as claimed in claim 1, in which the brominating agent is added, and the bromination carried out, at from 85 to 95° C.

4. A process as claimed in claim 1, in which an aqueous suspension is used which contains from 5 to 20% by weight, based on the suspension, of benzanthrone.

5. A process as claimed in claim 2, in which an aqueous suspension is used which contains from 10 to 15% by weight, based on the suspension, of benzanthrone.

6. A process as claimed in claim 3, in which an aqueous suspension is used which contains from 10 to 15% by weight, based on the suspension, of benzanthrone.

7. A process as claimed in claim 6, in which the mean particle size of the benzanthrone is from 20 to 30 $\mu$m.

8. A process as claimed in claim 1 wherein the bromine or brominating agent is added to the suspension uniformly over a period of about 1 to 4 hours maintaining the suspension at a temperature above 80° C. up to about 120° C.

9. A process as claimed in claim 8 carried out under a superatmospheric pressure sufficient to raise the temperature above the boiling point of water.

10. A process as claimed in claim 8, in which an aqueous suspension is used which contains about 10 to 15% by weight, based on the suspension, of benzanthrone.

* * * * *

UNITED STATES PATENT AND TRADEMARK OFFICE
CERTIFICATE OF CORRECTION

PATENT NO.  : 4,146,547
DATED       : March 27, 1979
INVENTOR(S) : Alfred Schuhmacher et al It is certified that error appears in the above-identified patent and that said Letters Patent are hereby corrected as shown below:

<u>IN THE CLAIMS</u>:

Claim 1, line 1, "Bz-1bromoben-..." should be

--- Bz-1-bromoben-... ---

Signed and Sealed this

*Twenty-fifth* Day of *December 1979*

[SEAL]

*Attest:*

SIDNEY A. DIAMOND

*Attesting Officer*   *Commissioner of Patents and Trademarks*